US008747446B2

(12) United States Patent
Chen et al.

(10) Patent No.: US 8,747,446 B2
(45) Date of Patent: Jun. 10, 2014

(54) HAIR RESTORATION CARING DEVICE

(76) Inventors: Chung-Yang Chen, Taipei County (TW); Craig Nabat, Irvine, CA (US)

( * ) Notice: Subject to any disclaimer, the term of this patent is extended or adjusted under 35 U.S.C. 154(b) by 157 days.

(21) Appl. No.: 13/166,902

(22) Filed: Jun. 23, 2011

(65) Prior Publication Data

US 2011/0251658 A1    Oct. 13, 2011

Related U.S. Application Data

(63) Continuation-in-part of application No. 12/577,239, filed on Oct. 12, 2009.

(51) Int. Cl.
*A61N 5/06* (2006.01)
(52) U.S. Cl.
CPC .................................. *A61N 5/0617* (2013.01)
USPC .............................................. 607/88; 607/89
(58) Field of Classification Search
CPC ............... A61N 5/0617; A61B 18/203; A61B 2018/00476
USPC .............................. 128/898; 607/88–94; 606/9
See application file for complete search history.

(56) References Cited

U.S. PATENT DOCUMENTS

| 6,497,719 | B2 * | 12/2002 | Pearl et al. ........................ 607/89 |
| 6,524,329 | B1 * | 2/2003 | Benedict ........................... 607/88 |
| 7,722,656 | B1 | 5/2010 | Segal |
| 2002/0188334 | A1 | 12/2002 | Carlgren |
| 2004/0147984 | A1 * | 7/2004 | Altshuler et al. ................ 607/88 |
| 2004/0153131 | A1 * | 8/2004 | Yorke ................................ 607/91 |
| 2005/0075703 | A1 * | 4/2005 | Larsen .............................. 607/88 |
| 2005/0107716 | A1 * | 5/2005 | Eaton et al. .................... 600/544 |
| 2006/0161226 | A1 | 7/2006 | McMickle |
| 2007/0255359 | A1 * | 11/2007 | Neev ................................ 607/90 |
| 2008/0125835 | A1 * | 5/2008 | Laurent ........................... 607/89 |
| 2008/0125836 | A1 | 5/2008 | Streeter et al. |
| 2010/0076529 | A1 | 3/2010 | Tucker et al. |
| 2010/0094384 | A1 | 4/2010 | De Taboada et al. |
| 2010/0106077 | A1 | 4/2010 | Rabin et al. |
| 2010/0242155 | A1 * | 9/2010 | Carullo, Jr. .................... 2/171.2 |
| 2011/0022132 | A1 | 1/2011 | Kim |
| 2011/0092863 | A1 | 4/2011 | Kim et al. |
| 2011/0160814 | A2 * | 6/2011 | Tucker et al. ................... 607/90 |

FOREIGN PATENT DOCUMENTS

| DE | G91 02 407.2 | * | 7/1991 |
| EP | 1 166 016 A1 | * | 7/2006 |
| GB | 2262043 A | | 9/1993 |
| JP | 10295767 A | | 10/1998 |
| RU | 2 114 544 C1 | * | 10/1998 |
| WO | WO95/19808 | | 7/1995 |
| WO | WO2006/078613 A3 | | 7/2006 |
| WO | WO2006/125367 A1 | | 11/2006 |
| WO | WO2009/131420 A3 | | 10/2009 |

* cited by examiner

*Primary Examiner* — Gary Jackson
*Assistant Examiner* — Nathan J Jenness
(74) *Attorney, Agent, or Firm* — WHGC, P.L.C.; John F. O'Rourke

(57) ABSTRACT

A hair restoration caring device includes a treatment hood, a suspension member and a hair caring device. The treatment hood is to be disposed over a user's head. The suspension member is fastened to the treatment hood. The hair caring device is attached to the suspension member and is movable with respect to the user scalp. The hair caring device includes an outer casing mounted slidably on the suspension member, and has several downward combing projections and several light emitters installed above the combing projections respectively for radiating light waves. Each combing projection is aligned with a respective light emitter and is formed with an axial passage to permit past through of light waves of the respective light emitter.

6 Claims, 14 Drawing Sheets

HAIR RESTORATION CARING DEVICE

CROSS-REFERENCE OF RELATED APPLICATION

This application is a Continuation-in-Part of U.S. patent application Ser. No. 12/577,239, which was filed on Oct. 12, 2009 and is presently pending.

BACKGROUND OF THE INVENTION

1. Field of the Invention

The present invention relates to a hair restoration caring device, more particularly to a hair restoration caring device, in which a plurality of light emitters are applied for radiating light waves toward a user's scalp, thereby enhancing hair restoration at the balding portion of the user's scalp.

2. Description of the Prior Art

Several treatments have been proposed or developed in order to solve the baldness at human scalp due to hair loss. One method is to apply a medication lotion over the balding part of a user's scalp. The medication lotion may consist of some expander to prevent blood cells called platelets from clumping together at the terminating ends of the blood vessels, thereby enhancing blood circulation and nutrition supply leading to hair restoration at the balding part of the user's scalp. Oral suspension is recommended as another method in order to control the balance of sex hormones and to prevent depauperation of the cell follicles. However, there exist some side effects when oral suspension is recommended, which and brings an unfavorable health condition to the user. Hair transplant surgery is suggested as a third method, which can restore one's initial hair style at the balding part but loss of hairs at the other part of the user's head may continue to occur. Hair grafting surgery is tremendously expensive and beyond the reach of an ordinary person.

Presently, a new hair treatment method has been developed, in which, a ray of 650 nm is applied to radiate at the user's scalp in order to enhance the blood circulation thereat such that blood cells are supplied with sufficient nutrition to enable hair regrowth at the balding part of the user's scalp. It is noted that the above-stated method is low in cost and does not bring side effects to the user.

Presently available infrared therapy apparatus for hair loss treatment is in a hood configuration, and generally includes a plurality of ray emitters distributed at an interior thereof. The hood must be disposed over the user's head, thereby covering the entire scalp such that the entire scalp is under the radiation of the ray emitters. The user may feel stuffy or discomfort when his entire scalp is constantly covered by the hood. In addition, the user may feel unwell if the entire scalp is put under the radiation for a long period of time.

A conventional infrared therapy apparatus is proposed, which includes a comb structure that needs to be gripped by the user's hand for disposing the ray emitters over the balding part of the user's scalp. After a period of gripping the comb structure for an extended period, the user may get fatigued so that he has no desire to repeat the combing operation, thereby rendering the conventional infrared therapy apparatus less useful.

SUMMARY OF THE INVENTION

Therefore, in order to solve the above-mentioned drawbacks, it is the object of the present invention to provide a hair restoration caring device including a hair caring device movable with respect to the user's scalp so that only a specific part of the scalp will be radiated, thereby avoiding the discomfort encountered during use of the conventional infrared therapy apparatus.

The hair restoration caring device of the present invention includes a treatment hood, a suspension member and a hair caring device. The treatment hood is to be disposed around a user's head. The suspension member is fastened to the treatment hood. The hair caring device is attached to the suspension member and is movable with respect to the user scalp. The hair caring device includes an outer casing mounted on the suspension member, and has a plurality of combing projections extending downwardly therefrom, and a plurality of light emitters installed within the outer casing above the combing projections respectively for radiating light waves. Each of the combing projections is aligned with a respective one of the light emitters and is formed with an axial passage to permit past through of light waves of the respective one of the light emitters toward the user's scalp.

Preferably, the suspension member includes first and second curved suspending rails spanning above the user's head and extending through the outer casing in such a manner to permit sliding action of the outer casing along the first and second curved suspending rails.

In one embodiment, the outer casing has an upper portion and a lower transparent portion. The combing projections extend downwardly from the lower transparent portion while the light emitters are installed respectively within the upper portion in alignment with the combing projections respectively.

The hair restoration caring device of the present invention further includes a driving unit meshed operably with at least one of the first and second curved suspending rails in such a manner that activation of the driving unit results in reciprocal and sliding movement of the outer casing along the at least one curved suspending rail, thereby irritating the user's scalp via the combing projections and simultaneously conducting scanning operation by the light waves emitted from the light emitters.

The hair restoration caring device of the present invention further includes a remote control for controlling activation and de-activation of the driving unit and for adjusting light emission time interval of the light emitters.

As explained above, the hair restoration caring device is movable with respect the user scalp and is capable of radiating only to the desired part of the scalp. There is no need for covering the entire scalp of the user's head, thereby avoiding the discomfort or stuffiness encountered during use of the conventional infrared therapy apparatus. Since only a portion of the light emitters is under operation at a time for radiating the desired part of the scalp while the remaining portion of the scalp is free from radiating, the user will not suffer from over irritation. In addition, the hair caring device is mounted by combination of the treatment hood and the suspension member so that the hair restoration caring device is not required to be held by the user's hand as in the prior art. Thus, the user of the present hair restoration caring device can do his daily or routine work without interference.

BRIEF DESCRIPTION OF THE DRAWINGS

Other features and advantages of this invention will become more apparent in the following detailed description of the preferred embodiments of this invention, with reference to the accompanying drawings, in which.

DETAILED DESCRIPTION OF THE PREFERRED EMBODIMENTS

Figure 1:
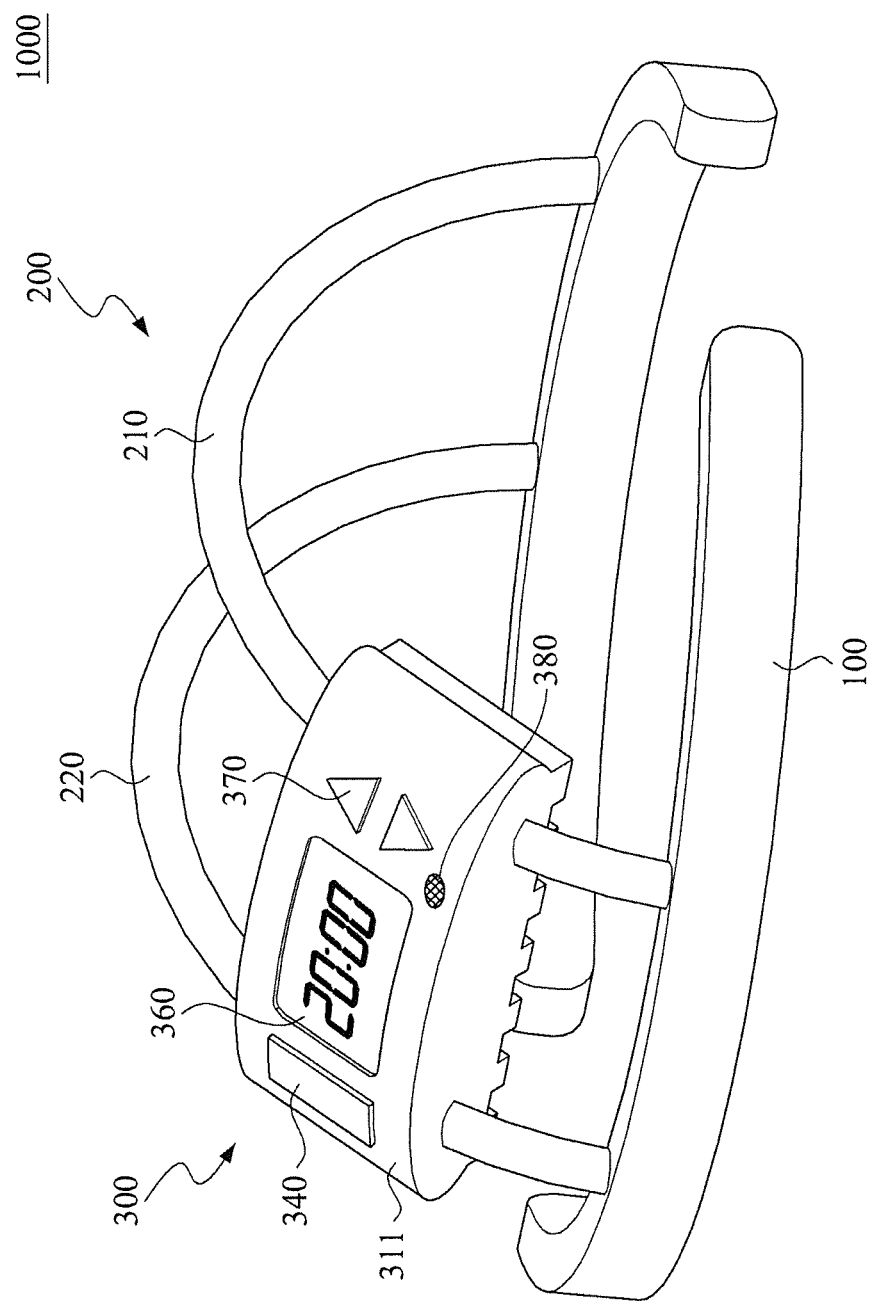
FIG. 1 is a perspective view of the first embodiment of a hair restoration caring device of the present invention.
Figure 2:
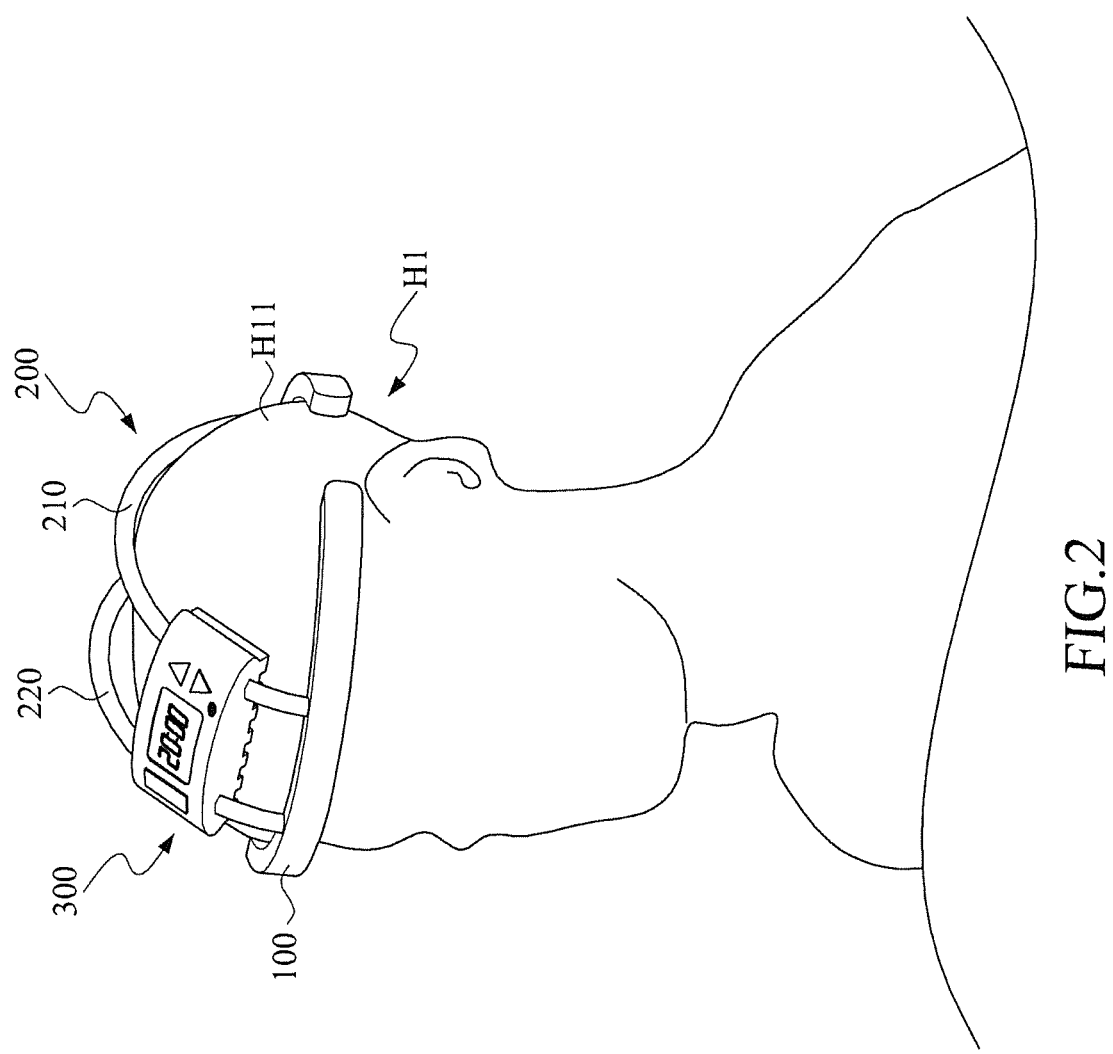
FIG. 2 shows the hair restoration caring device of the present invention disposed over a user's head.

FIG. 1 is a perspective view of the first embodiment of a hair restoration caring device 1000 of the present invention while FIG. 2 shows the hair restoration caring device 1000 of the present invention disposed over a user's head. As illustrated, the hair restoration caring device 1000 accordingly includes a treatment hood 100, a suspension member 200 and a hair caring device 300.

The treatment hood 100 is an adjustable curved structure and is adapted to be disposed around the user's head H1, as best shown in FIG. 2.

The suspension member 200 is fastened to the treatment hood 100 while the hair caring device 300 is attached to the suspension member 200. In this embodiment, the suspension member 200 is fastened securely to the treatment hood 100 while the hair caring device 300 is attached slidably on the suspension member 200.

The suspension member 200 includes first and second curved suspending rails 210, 220, in the form of rod structure. In this embodiment, the first and second suspending rails 210, 220 are curved ergonomically (in the form of rack to mesh with pinion or toothed wheels of a driving unit) so as to span over the top part H11 of the user's head H1. The first and second curved suspending rails 210, 220 have first and second ends fastened securely to the treatment hood 100 in such a manner that the first and second curved suspending rails 210, 220 extend through the hair caring device 300. Under this condition, the hair caring device 300 is slidable on the first and second suspending rails 210, 220, and is thus movable from a front portion of the top part H11 toward a rear portion of the top part H11 of the user's head H1.

In another embodiment, the suspension member 200 includes only the first suspending rail 210 and excluding the second suspending rail 220.

Referring again to FIGS. 1 to 4, wherein FIG. 3 is a cross-sectional view of the hair restoration caring device of the present invention shown in FIG. 1 while FIG. 4 is a block diagram illustrating the hair restoration caring device of the present invention. The hair caring device 300 further includes an outer casing 310, a plurality rows of light emitters 330, a start switch 340, a display screen 360, a regulator 370 and a buzzer 380.

Figure 3:
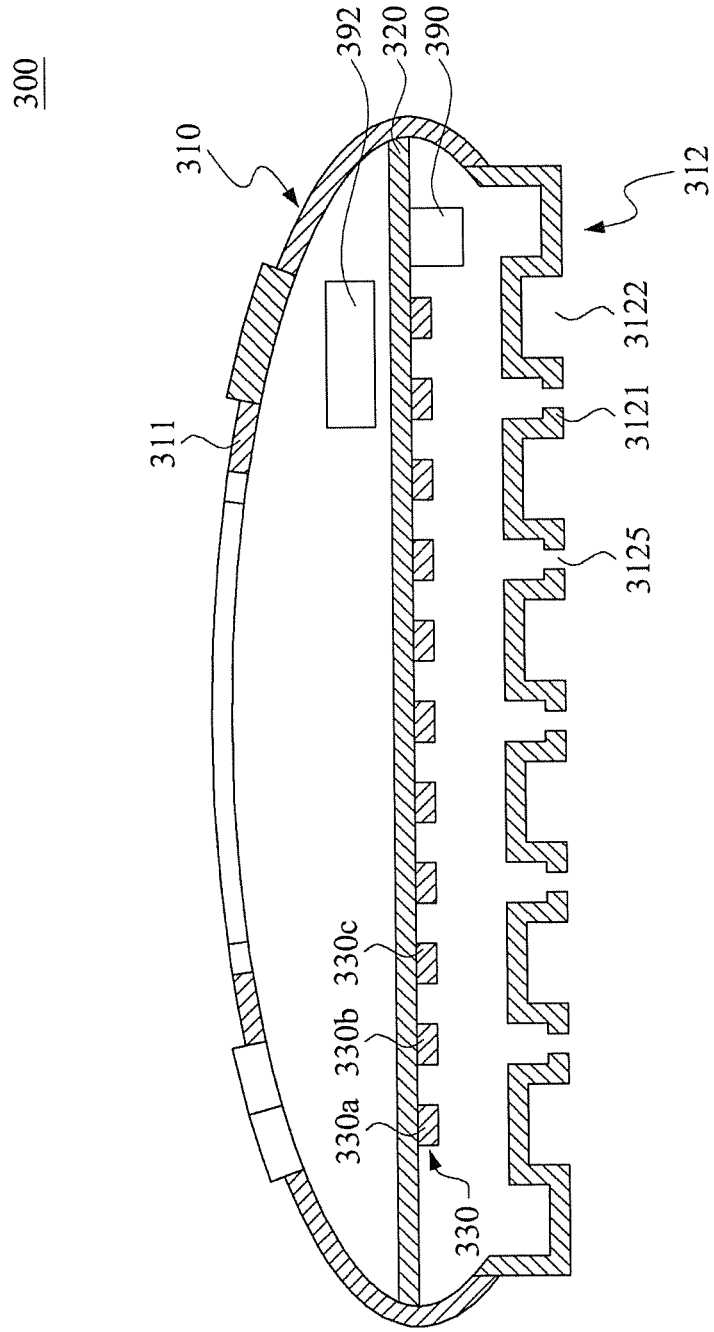
FIG. 3 is a cross-sectional view of the hair restoration caring device of the present invention shown in FIG. 1.
Figure 4:
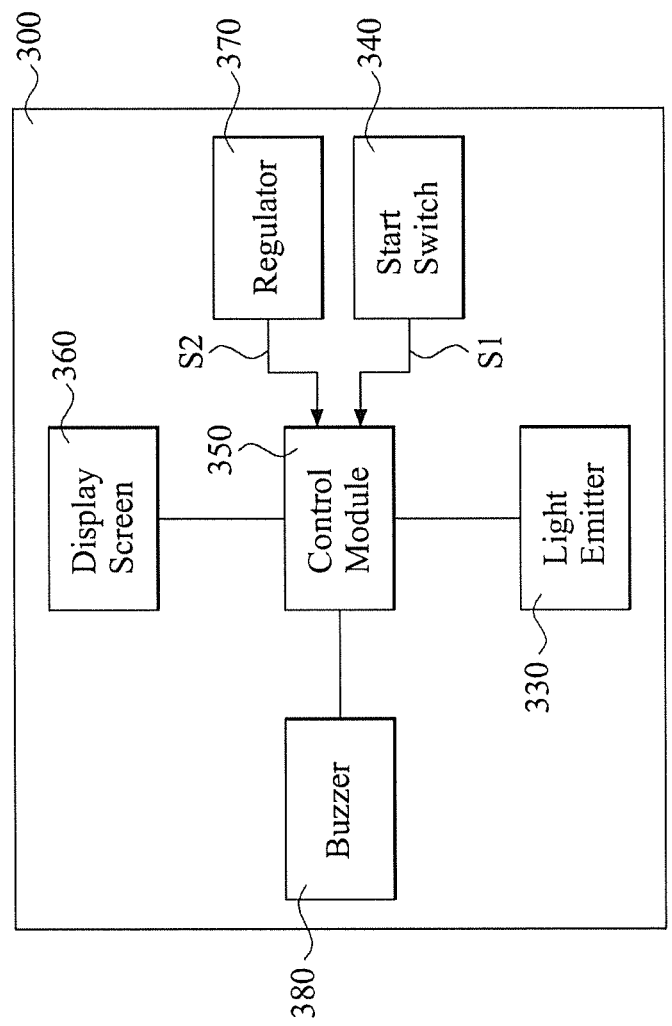
FIG. 4 is a block diagram illustrating the hair restoration caring device of the present invention.

As illustrated in FIG. 3, the outer casing 310 is a hollow structure, and has an upper portion 311 and a lower transparent portion 312 facing toward the user's head H1. The transparent portion 312 of the outer casing 310 is formed with a plurality rows of combing projections 3121 extending downwardly therefrom and a plurality of upward recessions 3122 spaced apart and alternately disposed from one another. The rows of light emitters 330 are installed within the upper portion of the outer casing 310 so as to be located above the rows of combing projections 3121 respectively. Each of the combing projections 3121 is formed with an axial passage 3125 to permit passage of light therethrough. A printed circuit board 320 is mounted within the outer casing 310.

Each of the light emitters 330 can be an LED (Light Emitting Diode) and is capable of emitting light wave for radiating toward the user's head H1 via the transparent portion 312 of the outer casing 310. In this embodiment, the light emitters 330 are mounted on the printed circuit board 320 and are directed toward the transparent portion 312 of the outer casing 310. Preferably, each of the combing projections 3121 in a respective row is aligned with a respective one of the light emitters 330 so that the light wave can be radiated toward the user's scalp H1 through the axial passage 3125 in the respective combing projection 3121. Note that the hair caring device 300 in the present embodiment further includes a driving unit 392 (see FIG. 3) adapted to be meshed with the first and second curved rails 210, 220 (see FIG. 2) via gear and pinion system, or other toothed wheels which are common in the driving unit in such a manner that activation of the driving unit 392 results in reciprocal and sliding movement of the outer casing 310 along the first and second curved suspending rails 210, 220, thereby irritating the user's scalp via the combing projections 3121 and simultaneously conducting light combing operation onto the user's scalp by the light waves emitted from the rows of light emitters 330. Note that during the reciprocal movement of the outer casing 310 along the first and second curved suspending rails 210, 220, the strands of hairs (if the user has any) are pressed downward towards the lateral sides by virtue of the periphery defining the distal end of a respective combing projection 3121, thereby forming a dermis path to permit direct light combing operation onto the dermis of the user's scalp by the light waves emitted from the rows of light emitters 330.

In the present embodiment, each light wave ranges from 600 nm to 1000 nm, which irritates cell follicles at the balding part of user's scalp so that hair regrowth at the balding part is possible. Thus, the hair restoration caring device of the present invention is capable of performing hair restoration at the balding part of the user's scalp. The light emitters 330 consist of a plurality of first light emitters 330a, a plurality of second light emitters 330b and a plurality of third light emitters 330c. Each of the first and second light emitters 330a, 330b is an LED (Light Emitting Diode) while each of the third light emitters 330c is a laser module. Note that each of the first, second and third light emitters 330a, 330b, 330c is arranged stagger to one another and generates light wave different from one another. For instant, the light wave generated by the first light emitter 330a ranges from 700 nm to 1000 nm and in this embodiment is 880 nm. The light wave generated by the second light emitter 330b ranges from 600 nm to 7000 nm, and in this embodiment is 660 nm. The light wave generated by the third light emitter 330c ranges from 600 nm to 7000 nm, and in this embodiment is 660 nm. When the balding part of the user's scalp is irritated by different light waves, hair regrowth at the balding part is further possible.

Referring again to FIG. 1, the start switch 340, the display screen 360, the regulator 370 and the buzzer 380 are mounted on the upper portion 311 of the outer casing 310. The start switch 340 is provided for activating the plurality of light emitters 330. The display screen 360 is intended for displaying a time set for operation of the plurality of light emitters 330 while the regulator 370 is used for regulating an amount of the time set for operation of the plurality of light emitters 330. The buzzer 380 is capable of generating an alarm at a predetermined time interval to remind the user.

Referring again to FIG. 4, the hair restoration caring device further includes a control module 350 preferably a microprocessor, coupled electrically to the start switch 340, the display screen 360, the regulator 370 and the buzzer 380 in such a manner that activation of the start switch 340 generates an ON signal S1 transmitted to the control module 350. Upon receipt of the ON signal S1, the control module 350 will activate the light emitters 330 to emit light waves and the display screen 360 displays the set time for operation of the light emitters 330 (or radiating time), thereby counting the set time to the last minute. In FIG. 1, the operation time of the light emitters 330 is [20:00], i.e., 20 minutes. Thus, when 1 minute passed by, the control module 350 adjusts the set time as [19:59], and upon reaching the set time [00:00], the control module 350 will de-activate the light emitters 330 and electrical supply to the display screen 360 is simultaneously disconnected. At this time, the buzzer 380, being connected to the control module 350, gives out an alarm at a predetermined time interval, reminding the user of the hair restoration caring device of the present invention that radiation of the light emitters 330 is approaching the set time. For instant, if the time interval is set at 5 minutes, that is [15:00], [10:00], [5:00] and [0:00], the control module 350 will activate the buzzer 380 to give out alarm at 5 minute interval and the ending alarm at [0:00] is significantly different from the other, informing the user completion of application of the hair restoration caring device of the present invention.

The user can adjust the set time with assistance of the regulator 370. When the regulator 370 is rotated to set the desired time, an adjust signal S2 is transmitted to the control module 350. Upon receipt of the adjust signal S2, the control module 350 will display the radiation time over the display screen 360. For instant, the radiation time is adjusted from [20:00] to [15:00], i.e., the radiation time is set for 15 minutes. Alternately, a wireless remote control can be configured in such a manner to have the function property of the control module for serving the purpose of the control module. Under this condition, the remote control is wirelessly connected to the start switch 340, the display screen 360, the regulator 370 and the buzzer 380 and the light emitters 330. The user can thus remotely control the above mentioned activity via the remote control. In addition, the remote control is also configured to control activation and de-activation of the driving unit 392 (see FIG. 3) and for adjusting light emission time interval of the light emitters 330. In one embodiment of the present invention, the driving unit 392 (see FIG. 3) can be excluded in order to economize the cost production. Under this condition, when it is desired to move the outer casing 310 along the first and second curved suspending rails 210, 220 to a desired position can be conducted manually.

Figure 10A:
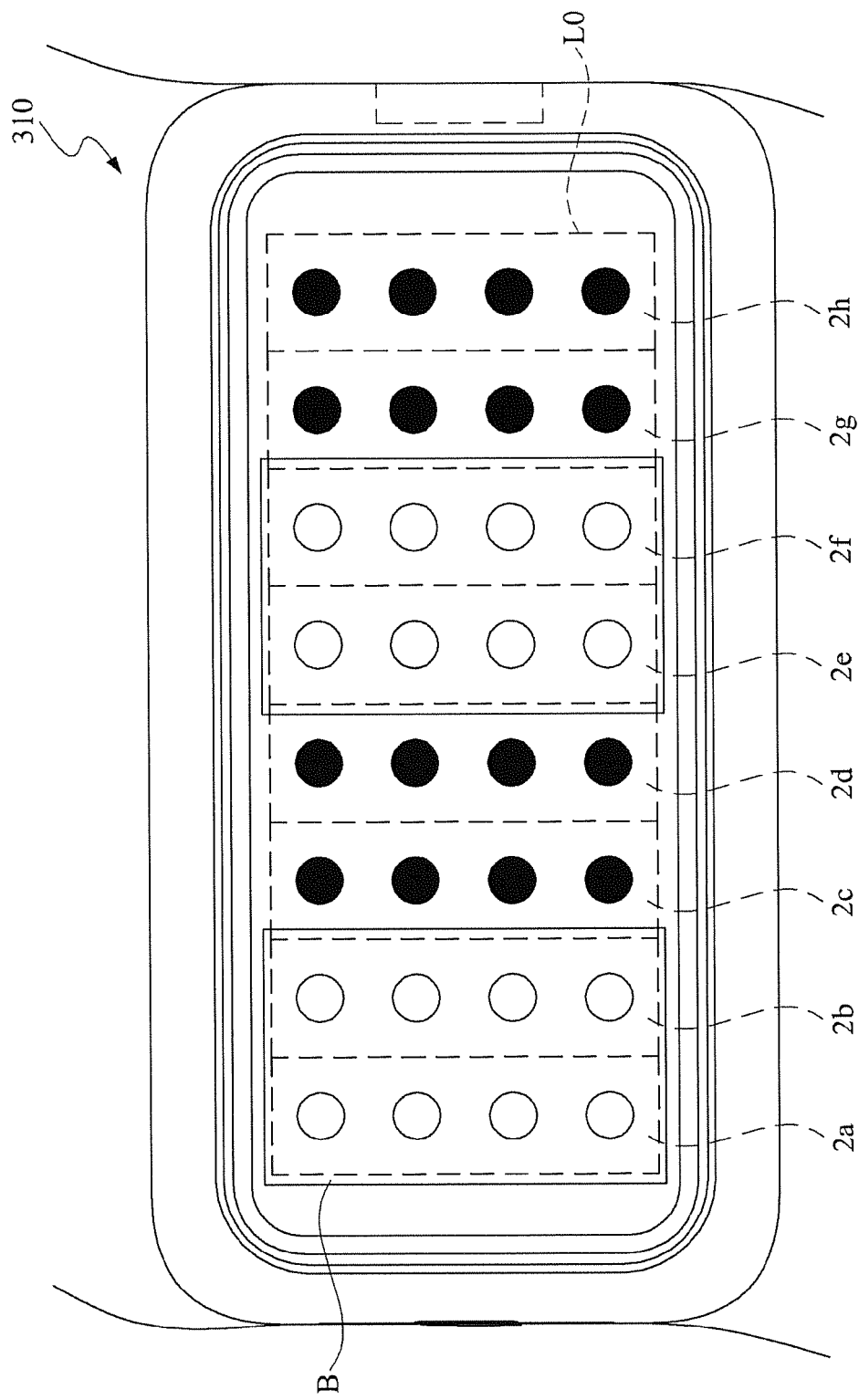
FIGS. 10A, 10B, 10C and 10D respectively show activation the light emitters in different patterns in the hair restoration caring device of the present invention.
Figure 10B:
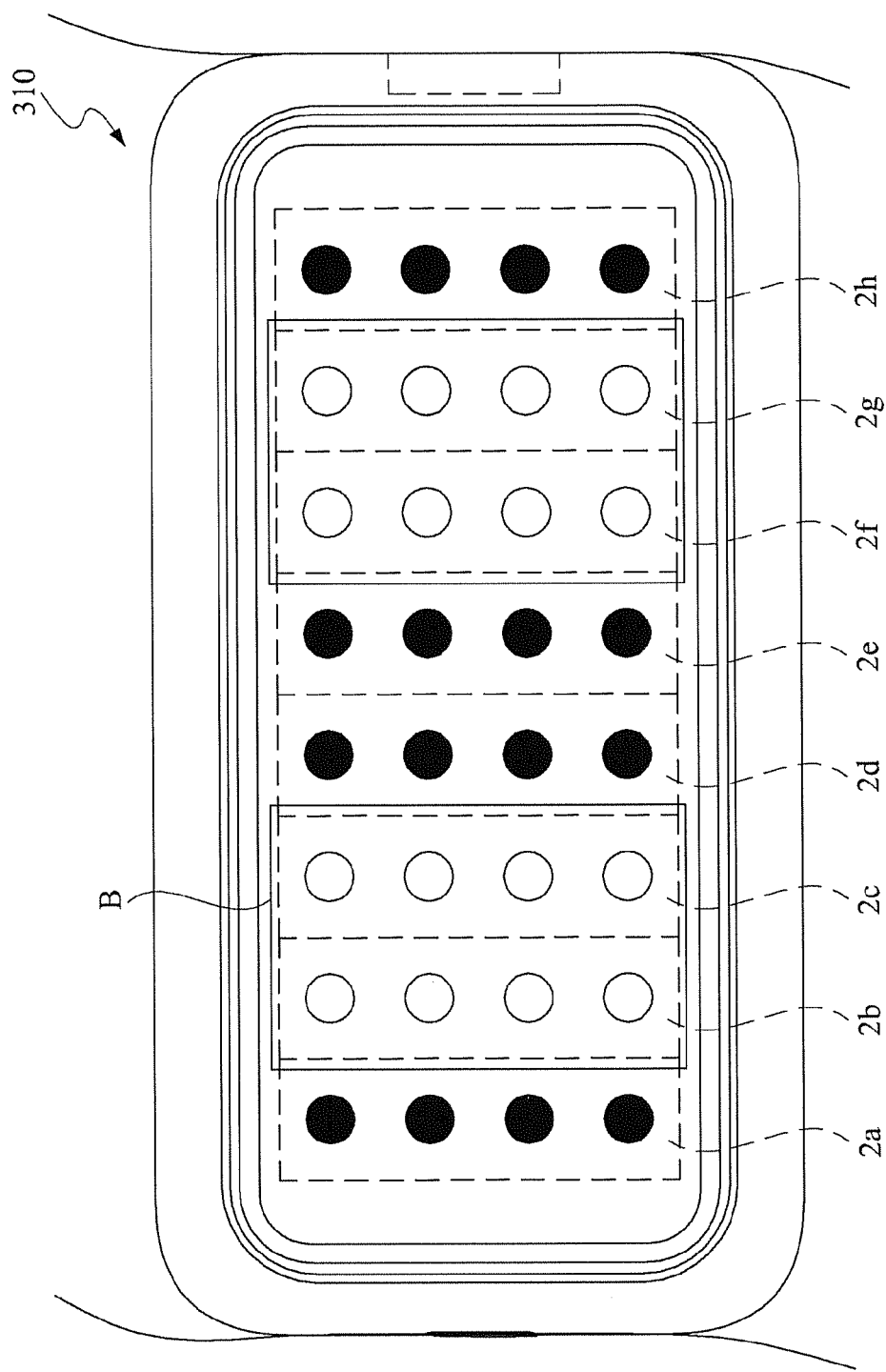
Figure 10C:
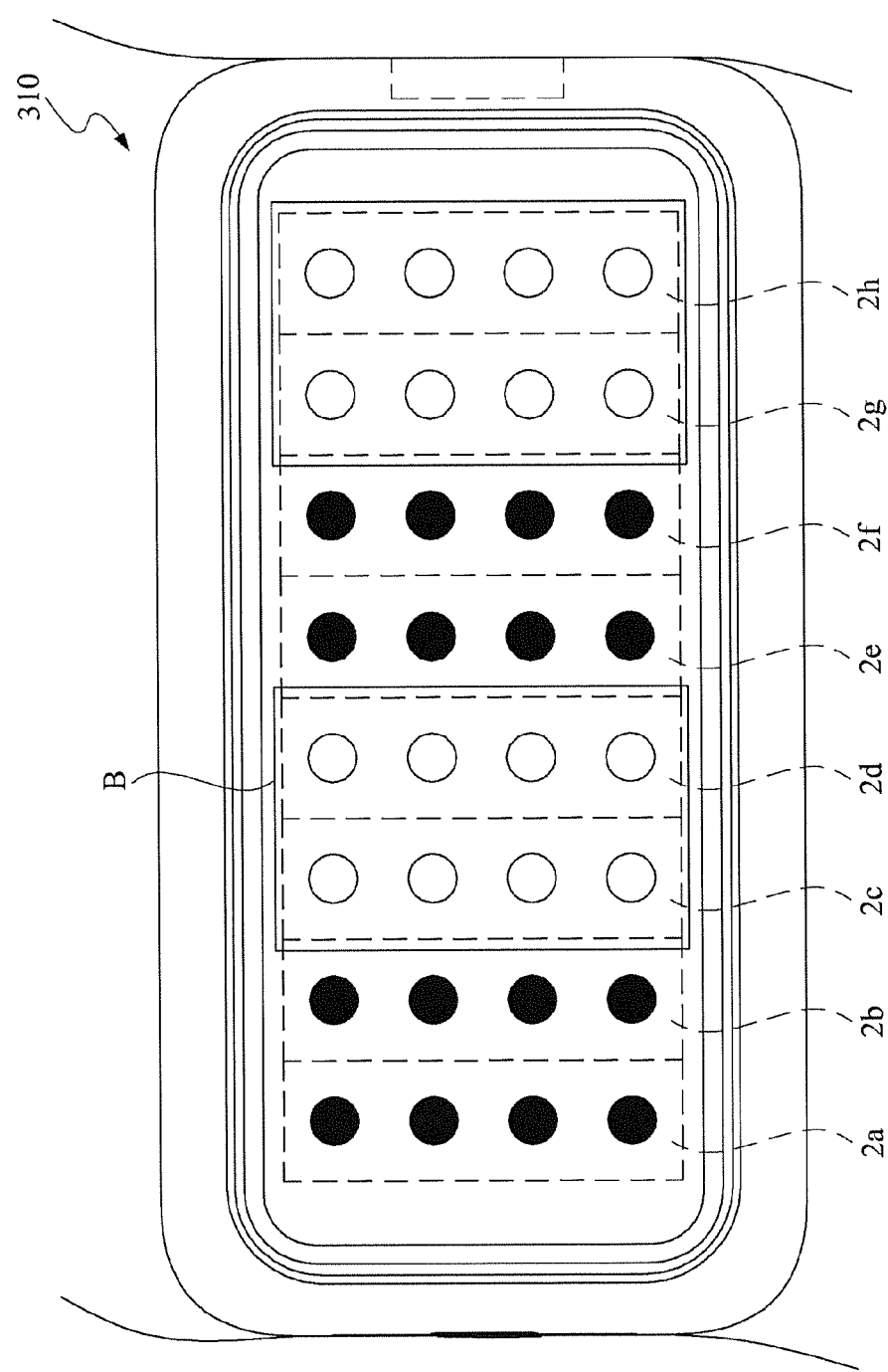
Figure 10D:
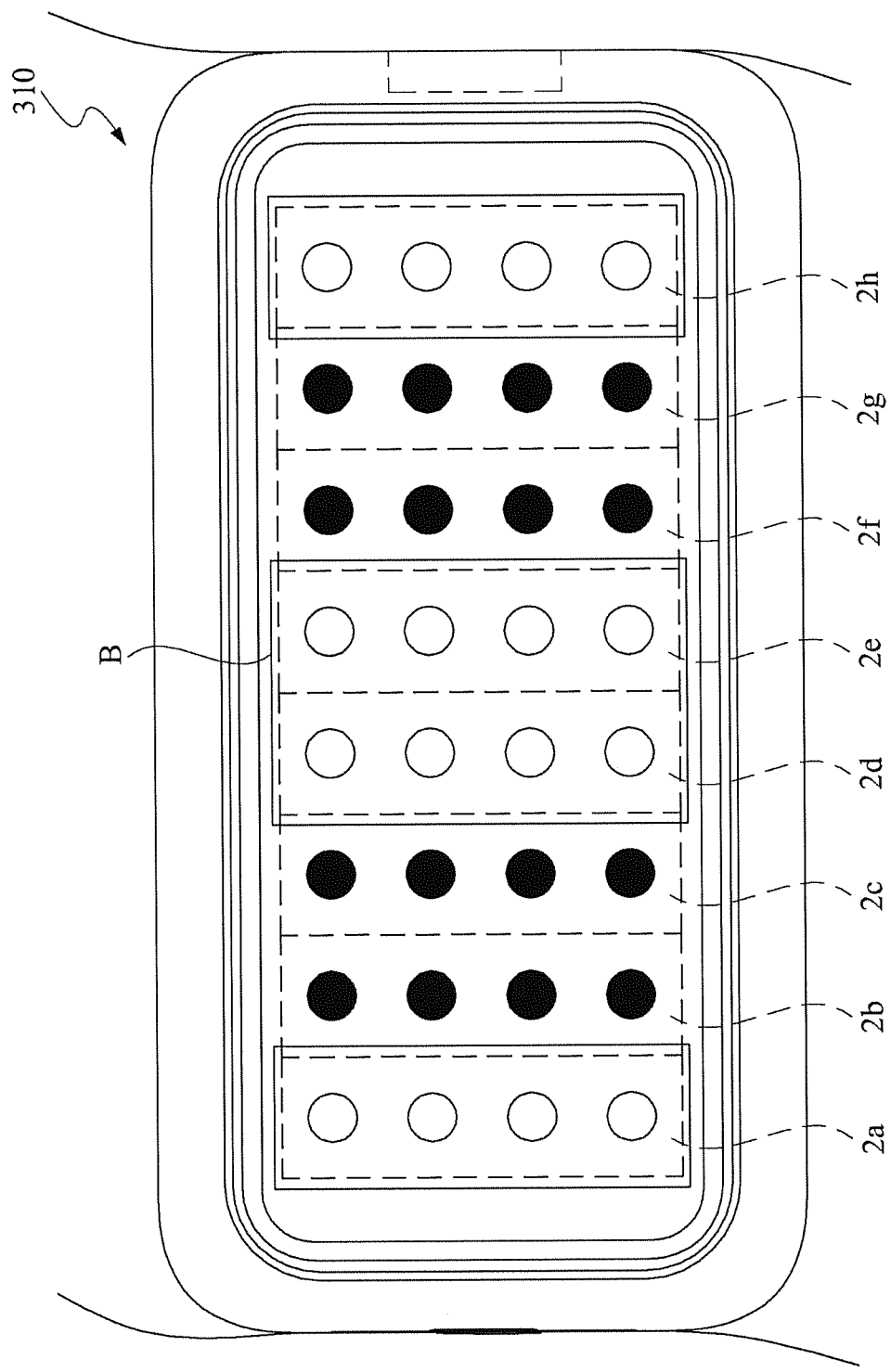

In addition to the first, second and third light emitters 330a, 330b, 330c, the light emitters 330 of the hair caring device 300 of the present invention further includes a plurality rows of light emitters 2a, 2b, 2c, 2d, 2e, 2f, 2g, 2h, installed respectively within the outer casing 310 in a parallel manner, as best shown in FIG. 10A, such that each row is spaced apart from an adjacent row in a predetermined gap, wherein the rows of the light emitters 2a, 2b, 2c, 2d, 2e, 2f, 2g, 2h are configured in such a manner to emit light waves in a predetermined patterns, thereby resulting in the light combing effect toward a user's scalp placed underneath the outer casing. Preferably, the plurality rows of the light emitters 2a, 2b, 2c, 2d, 2e, 2f, 2g, 2h include odd and even rows, which are configured in such a manner that the odd and even rows of the light emitters 2a, 2b, 2c, 2d, 2e, 2f, 2g, 2h emit light waves alternately and sequentially so as to result in the light combing effect toward the user's scalp. Alternately, as best shown in FIGS. 10A, 10B, 10C and 10D, wherein FIGS. 10A, 10B, 10C and 10D respectively show the rows of the light emitters 2a, 2b, 2c, 2d, 2e, 2f, 2g, 2h in activation in different predetermined patterns in the hair restoration caring device of the present invention. As illustrated in FIG. 10A, the regions marked by "B" (constituting four rows of light emitters 2a, 2b, 2e and 2f) are under operation, i.e., conducting the light combing operation onto the user's scalp while the regions marked by "LO" (constituting other four rows of light emitters 2c, 2d, 2g and 2h) are under the suspending state. As illustrated in FIG. 10B, the regions marked by "B" (constituting four rows of light emitters 2b, 2c, 2f and 2g) are under operation, i.e., conducting the light combing operation onto the user's scalp while the remaining regions (constituting other four rows of light emitters 2a, 2d, 2g and 2h) are under the suspending state. As illustrated in FIG. 10C, the regions marked by "B" (constituting four rows of light emitters 2c, 2d, 2g and 2h) are under operation, i.e., conducting the light combing operation onto the user's scalp while the remaining regions (constituting other four rows of light emitters 2a, 2b, 2e and 2f) are under the suspending state. As illustrated in FIG. 10D, the regions marked by "B" (constituting four rows of light emitters 2a, 2d, 2e and 2h) are under operation, i.e., conducting the light combing operation onto the user's scalp while the remaining regions (constituting other four rows of light emitters 2b, 2c, 2f and 2g) are under the suspending state.

Figure 10E:
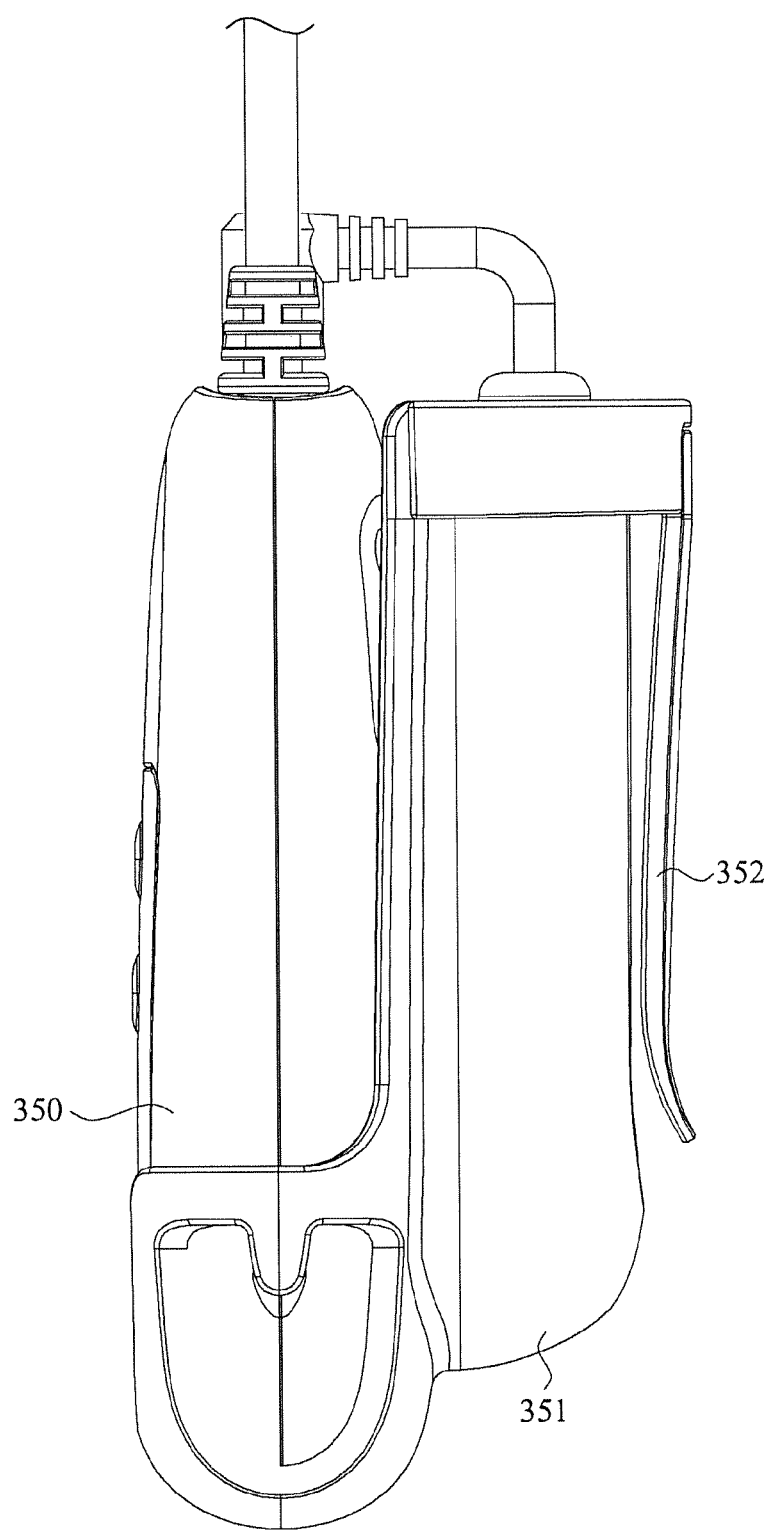
FIG. 10E shows a lateral side view of the remote control for controlling the activation of the hair restoration caring device of the present invention.

The present hair restoration caring device further includes a sensor unit 390 connected electrically or wirelessly to the remote control 350 (or the control module) (see FIG. 4) for detecting presence of the treatment hood 100 over the user's head H1. The sensor unit 390 is an infrared sensor device coupled electrically to the hair caring device 300 in such a manner that the sensor unit 390 may generate infrared ray for detecting light waves emitted by the light emitters 330, thereby ensuring presence of the hair restoration caring device over the user's head H1. In case, the sensor unit 390 is unable to detect the light waves emitted by the light emitters 330, a stop signal is generated and transmitted to the remote control 350, which, in turn, de-activate the light emitters 330. In the event, the sensor unit 390 detects the light waves of the light emitters 330; the remote control (or the control module) 350 will activate the light emitters 330 to precede the operation thereof until to the set time. Preferably, the remote control 350 is equipped with either a battery or a rechargeable battery 351 for power. Moreover, a clip (see FIG. 10E) is attached to the remote control 350 to facilitate the user to clip the remote control 350 onto his or her belt so that the problem of misplacing the remote control 350 at an undesired place can be avoided.

The sensor unit 390 is installed on the treatment hood 100, the suspension member 200 or within the hair caring device 300, the installation position thereof is not restricted in the present invention.

Figure 5:
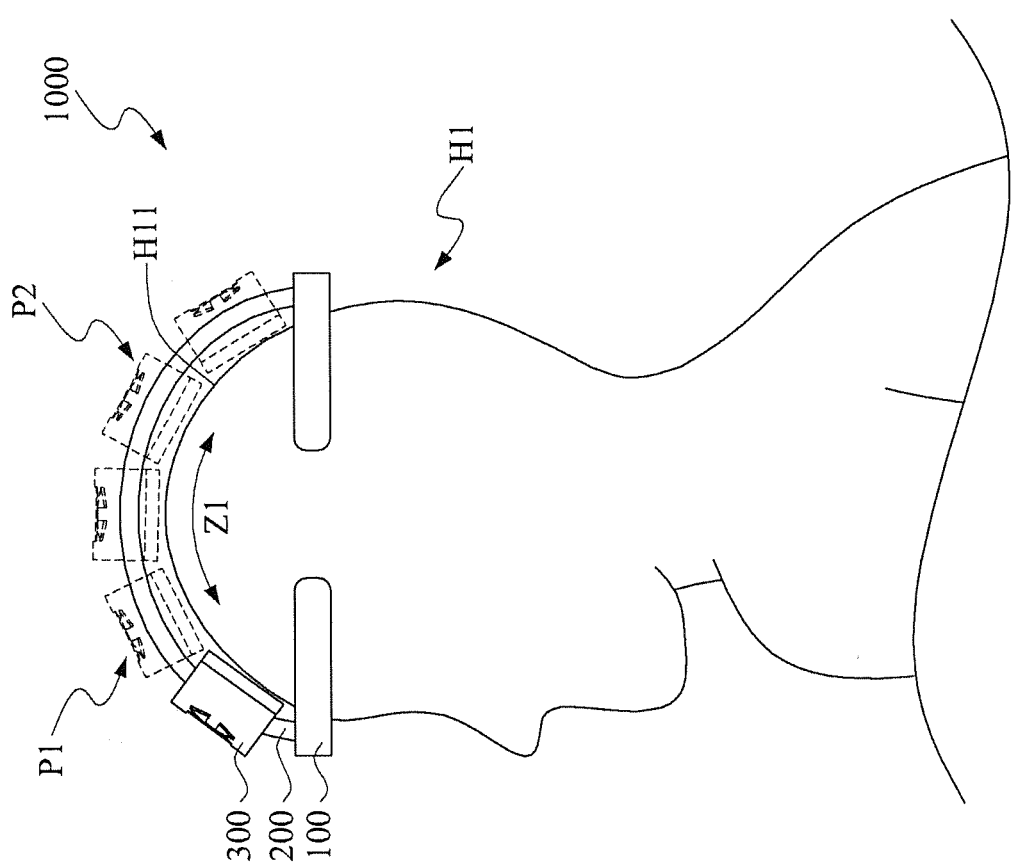
FIG. 5 shows the second embodiment of the hair restoration caring device of the present invention disposed over a user's head.

Referring to FIG. 5, the hair caring device 300 is arranged to shift from one spot to the other on the user's head H1 upon generation of each alarm so as to radiate the different parts of the balding scalp H11. Generally speaking, balding usually occurs at two sides of the forehead near the ears, beginning from the front part to the rear part so that balding due to hair loss at the scalp is easily visible.

When the hair restoration caring device 1000 is applied, those part near the ears is not required for radiation so that the overall weight thereof can be reduced. Since balding in one person differs from the other, radiation should be concentrated to the balding part of the user scalp. For instant, the hair caring device 300 is shifted between the positions P1 and P2 in order to concentrate the radiation onto the part Z1 as shown in FIG. 5. Since the hair caring device 300 of the present invention can be arranged to concentrate only on the desired balding part of the user scalp, the problem of covering the entire head and causing discomfort as encountered in the prior art can be avoided. In other words, the non-radiated part or the non-required part of the balding part of the user scalp get full rest during radiation to the desired balding part of the user scalp, irritation or over irritation at the user scalp can be avoided.

Figure 6:
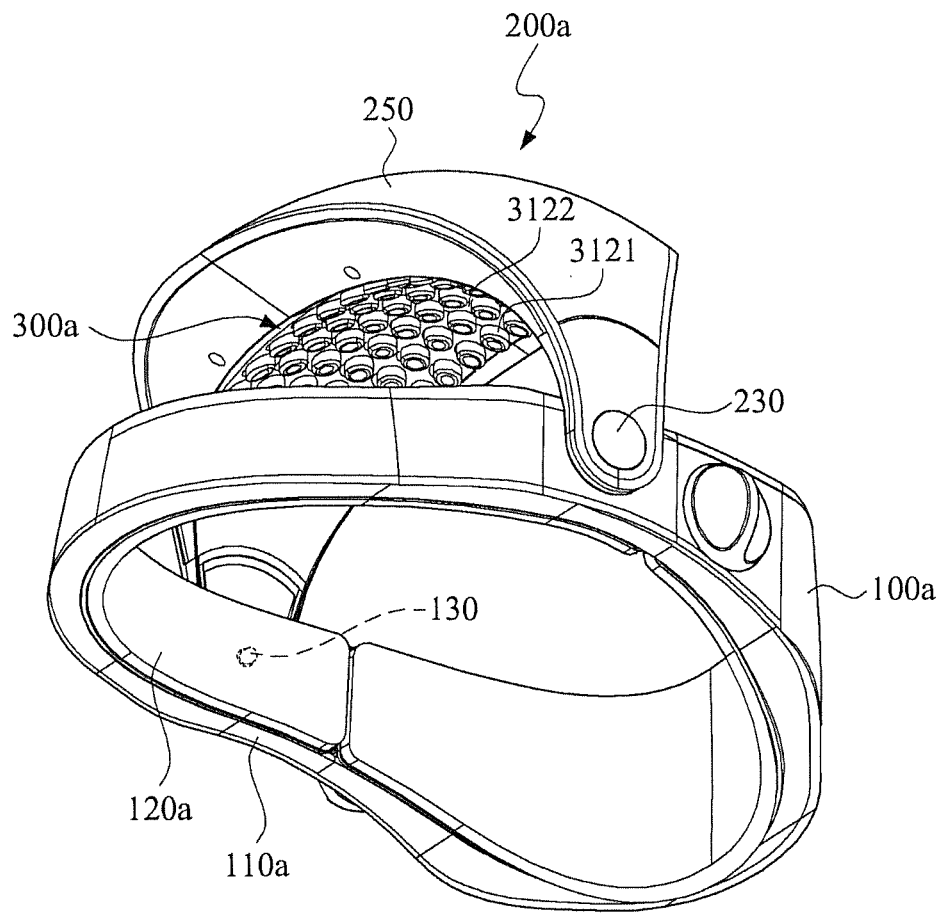
FIG. 6 is a perspective view of the second embodiment of the hair restoration caring device of the present invention.
Figure 7:
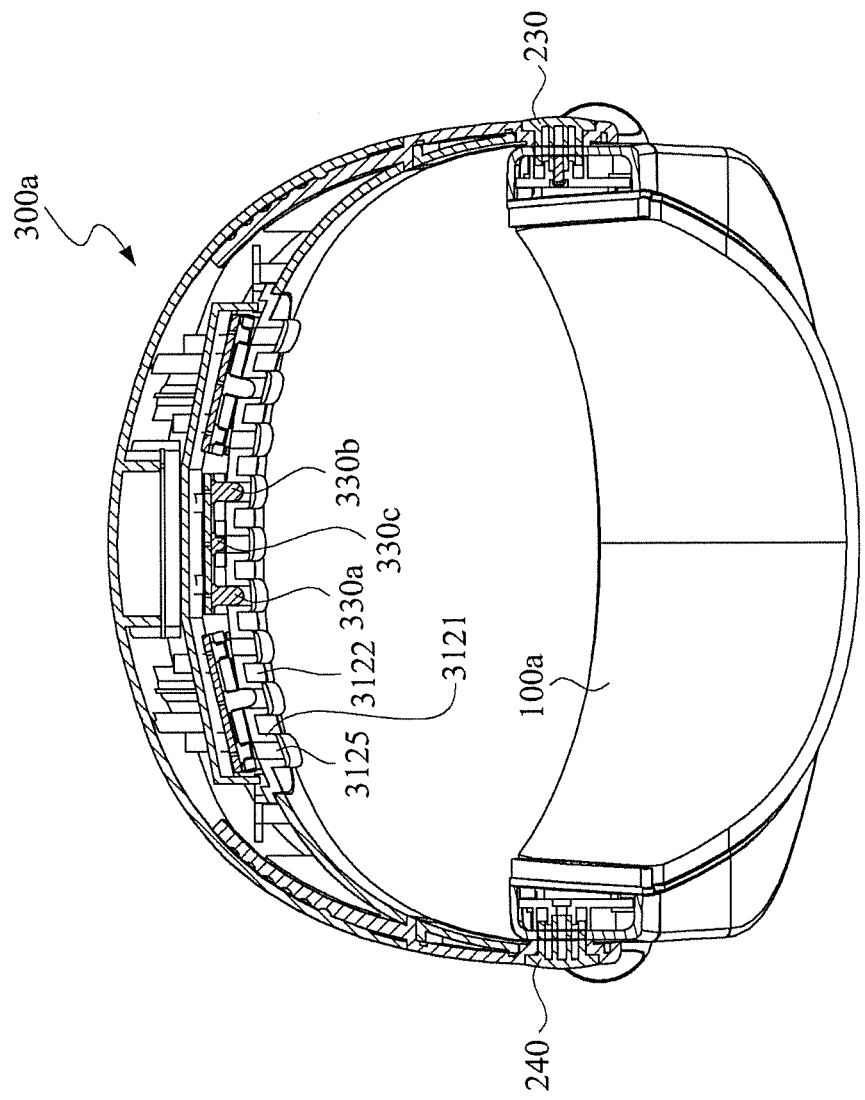
FIG. 7 is a cross-sectional view of the second embodiment of the hair restoration caring device of the present invention shown in FIG. 6.
Figure 8:
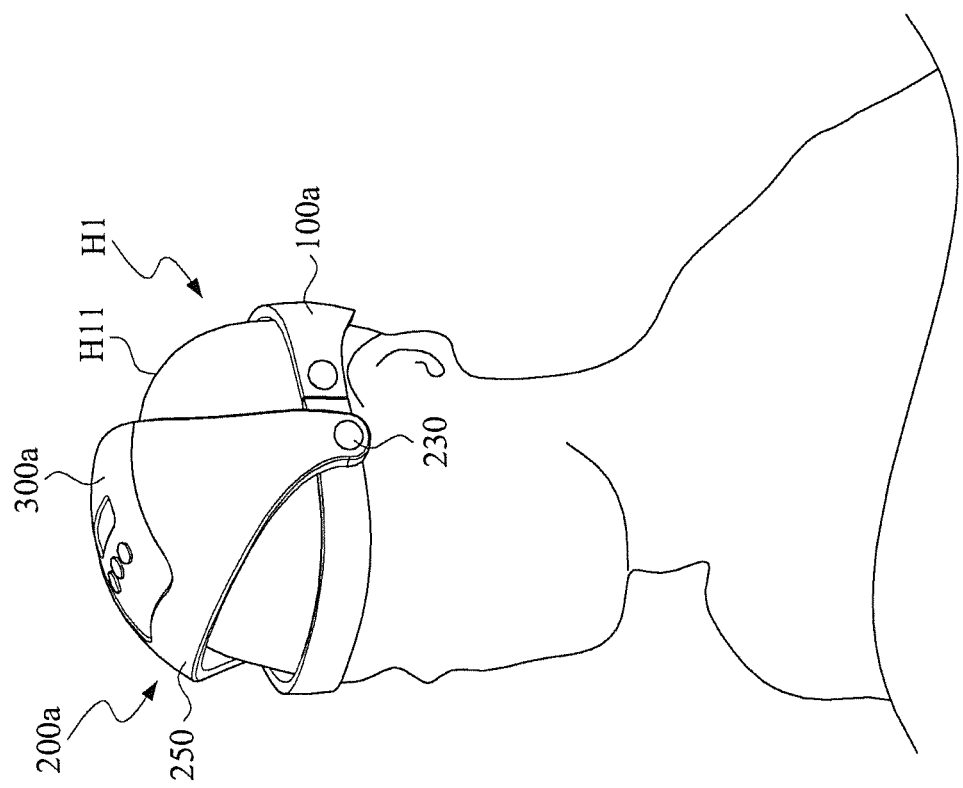
FIGS. 8 and 9 respectively show the second embodiment of the hair restoration caring device of the present invention disposed over the user's head in two conditions.

Referring to FIGS. 6 to 8, wherein FIG. 6 is a perspective view of the second embodiment of the hair restoration caring device of the present invention, FIG. 7 is a cross-sectional view of the second embodiment of the hair restoration caring device of the present invention shown in FIG. 6 while FIG. 8 shows the second embodiment of the hair restoration caring device of the present invention disposed over the user's head. The only difference with respect to the previous embodiment resides in that the suspension member 200a of the second embodiment includes a safety portion 250 (see FIG. 7) having first and second ends 230, 240 pivotally connected to two symmetric sides of the safety portion 250 (left and right sides of the user's head H1) such that the latter span over the top part H11 of the user's head H1. Note that the hair caring device 300a is installed interior to the safety portion 250 (see FIG. 6) in such a manner to face one lateral side of the user's head H1 with the combing projections 3121 directing toward the lateral side in an array manner.

The second embodiment further includes a forehead protection member 120a generally made from elastomeric material and fixed within the outer casing 110a to provide and cushion the user's forehead when impacted and a resilient switch button 130 installed within the outer casing 110a.

The resilient switch button 130 is electrically connected to the hair caring device 300 in such a manner that the control module 350 de-activates the light emitters 330 when no external force is applied on the resilient switch button 130. In other words, when an external force is applied on the switch button 130 due to wearing of the device over the user's head H1, the control module 350 activate the light emitters 330 to emit light waves therefrom for radiating onto the balding part of the user scalp. The resilient switch button 130 can be substituted by the sensor unit 390 of the previous embodiment. In the same manner, the sensor unit 390 of the previous embodiment can be replaced by the resilient switch button 130 of the second embodiment.

Figure 9:
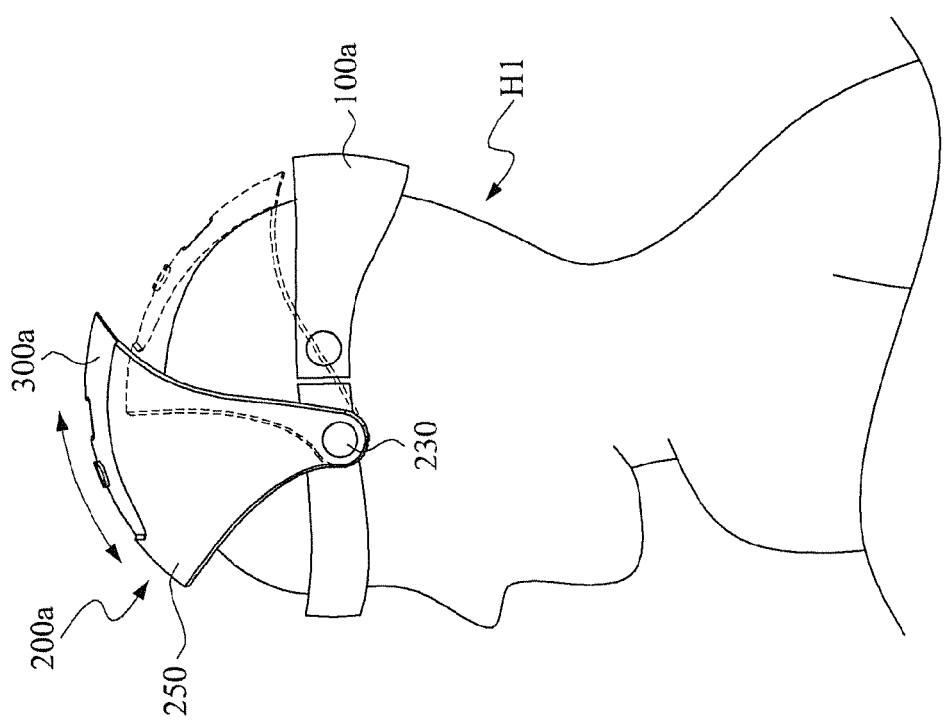

FIG. 9 shows the second embodiment of the hair restoration caring device of the present invention disposed over the user's head in another condition, wherein the user can rotate the suspension member 200a with respect to the treatment hood 100 so as to shift the hair caring device 300a from one place to the other for radiating the light waves to different parts of the user balding scalp.

While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A hair restoration caring device comprising:
a treatment hood having an adjustable curved contact structure adapted to be disposed around a circumference of a user's head above a user's ears;
a suspension member fastened to the treatment hood; and
a hair caring device including an outer casing mounted on the suspension member, the outer casing having an upper portion, and a lower transparent portion facing the user's scalp, the hair caring device having a plurality of hollow downward combing projections spaced apart and alternately disposed in the transparent portion between a plurality of spaced apart and alternately disposed upward recessions, the upper recessions bounded by the lower transparent portion, a plurality of light emitters disposed on the upper portion and facing the user's scalp, the downward combing projections each aligned with a respective light emitter and each having an axial passage through the lower transparent portion to permit the passage of light from the light emitter therethrough, the upper recessions each aligned with a respective light emitter, the light from the respective light emitter passing through the lower transparent portion to the user's scalp, the plurality of light emitters including a plurality of first light emitters, a plurality of second light emitters, and a plurality of third light emitters, each of the plurality of first, second and third light emitters being arranged staggered with respect to one another and each of the plurality of first, second and third light emitters generating a respective light wave frequency different from one another, wherein the plurality of light emitters are arranged in rows, wherein said rows of said light emitters are disposed in such a manner to emit light waves in a predetermined pattern, wherein the plurality of rows of the light emitters emit light waves so as to result in a direct light combing effect toward the user's scalp wherein the outer casing is slidable on the suspension member and is movable from a front portion toward a rear portion of the user's head and wherein the suspension member includes first and second curved suspending rails spanning above the user's head and extending through the outer casing in such a manner to permit sliding action of the outer casing along the first and second curved suspending rails.

2. The hair restoration caring device according to claim 1, wherein the combing projections extending downwardly from the lower transparent portion and the upward recessions are substantially flush with the lower transparent portion while the plurality of light emitters are installed respectively within the upper portion in alignment with the combing projections and the upward recessions respectively.

3. The hair restoration caring device according to claim 2, wherein the hair caring device further includes a driving unit meshed operably with at least one of the first and second curved suspending rails in such a manner that activation of the driving unit results in reciprocal and sliding movement of the outer casing along the at least one of the first and second curved suspending rails, thereby irritating the user's scalp via the combing projections and simultaneously conducting scanning operation by light waves emitted from the light emitters.

4. The hair restoration caring device according to claim 3, further comprising a remote control for controlling activation and de-activation of the driving unit and for adjusting a light emission time interval of the light emitters.

5. The hair restoration caring device according to claim 4, wherein the remote control is equipped with either a battery or a rechargeable battery for power.

6. A hair restoration caring device comprising:
a treatment hood adapted to be disposed around a portion of a user's head above a user's ears;
a suspension member fastened to the treatment hood, the suspension member including first and second curved suspending rails spanning above the user's head,
a hair caring device including an outer casing slidably mounted on the suspension member, wherein the first and second curved rails extend through the outer casing of the suspension member in such a manner to permit sliding action of the outer casing along the first and second curved suspending rails, the outer casing having a plurality of upward recessions, and hollow combing projections extending downwardly therefrom, and a plurality of light emitters installed within the outer casing for radiating light waves through each of the upward recessions and hollow combing projections respectively, each of the upward recessions and hollow combing projections being aligned with a respective one of the plurality of light emitters and the hollow combing projections being formed with an axial passage to permit the passage of direct light waves from the respective one of the plurality of light emitters toward the user's scalp; and
a remote control coupled to the hair caring device and disposed to cause light waves to be emanated by the hair caring device to the scalp, and to adjust a light emission time interval of the plurality of light emitters, wherein the plurality of light emitters includes a plurality of first light emitters, a plurality of second light emitters, and a plurality of third light emitters, each of the plurality of first, second and third light emitters being arranged staggered with respect to one another, and each of the plurality of first, second and third light emitters generates a light wave having a respective frequency different from one another, and wherein light emitters form a plurality of rows which are disposed in such a manner that the plurality of rows emit light waves so as to result in a direct light combing effect toward the user's scalp.

* * * * *